United States Patent [19]
Prescott

[11] Patent Number: 5,741,246
[45] Date of Patent: Apr. 21, 1998

[54] METHOD AND APPARATUS FOR LASER BALLOON ANGIOPLASTY TREATMENT OF MEDICAL CONDITIONS

[76] Inventor: Marvin A. Prescott, 833 Moraga Dr., Ste. 15, Los Angeles, Calif. 90049

[21] Appl. No.: 632,630

[22] Filed: Apr. 15, 1996

[51] Int. Cl.⁶ ..................... A61B 17/36
[52] U.S. Cl. ..................... 606/7; 606/15
[58] Field of Search ............... 606/2, 7, 9, 10, 606/11, 12, 14, 15, 16, 17

[56] References Cited

U.S. PATENT DOCUMENTS 4,881,547  11/1989  Danforth ..................... 606/194
5,370,615  12/1994  Johnson ..................... 604/96
5,470,352  11/1995  Rappaport ..................... 607/101

OTHER PUBLICATIONS

"GaInAsP/AlGaInP-Based Near-IR (780nm) Vertical-Cavity Surface-Emitting Lasers," by R.P. Schneider, Jr. et al., Electronics Letters, 30 Mar. 1995, vol. 31, No. 7, pp.554–555.

Primary Examiner—John P. Lacyk
Assistant Examiner—Sonya Harris-Ogugua
Attorney, Agent, or Firm—Graham & James LLP

[57] ABSTRACT

A laser balloon catheter device includes a housing containing a guidewire and an inelastic balloon. The balloon is surrounded by a clear silicone sleeve. A series of polyester electrically conductive flexible film strips are embedded inside the sleeve and adjacent the balloon. Each strip contains several vertical cavity surface-emitting lasers, each operating at 760–780 nanometer wavelengths and 1–10 milliwatts of power. During a balloon angioplasty procedure, the device is inserted into an affected artery across a region of stenosis. The balloon is inflated using inflation fluid provided from an external source. The inflated balloon expands the artery to eliminate the stenosis. Power is simultaneously applied to the lasers for a period of 5–10 minutes to encourage healing of the artery and reduce the occurrence of restenosis.

22 Claims, 3 Drawing Sheets

METHOD AND APPARATUS FOR LASER BALLOON ANGIOPLASTY TREATMENT OF MEDICAL CONDITIONS

BACKGROUND OF THE INVENTION

1. Field of the Invention

The present invention relates to a method and apparatus for balloon angioplasty treatment of medical conditions. More particularly, the present invention is directed to an apparatus for applying laser beam energy in a medical treatment regimen using a balloon angioplasty device in conjunction with electrically conductive flexible strips containing vertical cavity surface-emitting lasers capable of delivering a concentrated application of laser beam energy to a treatment area of an artery wall in a cost-effective and efficient manner.

2. Background

Balloon angioplasty is a known method for removing arteriosclerotic plaque from the lumen of affected arteries. At the outset of a routine percutaneous transluminal coronary angioplasty procedure, a preshaped angioplasty guiding catheter containing a balloon catheter equipped with a flexible intracoronary guidewire is engaged within the ostium of a coronary vessel containing the lesion to be dilated. Once suitably engaged (for example, within the left main or right coronary ostium), the guidewire is advanced within the lumen of the appropriate vessel and manipulated across the region of stenosis (narrowing). By rotating the guidewire, which contains a slight bend within its distal aspect, the operator can control the course of the wire, selecting the appropriate coronary lumen as the wire is advanced.

Once the wire is positioned across the region of stenosis, the angioplasty dilatation balloon catheter is advanced over the guidewire and positioned across the stenotic lesion. The angioplasty is accomplished by inflating the dilatation catheter to a high pressure, typically 6 to 10 atmospheres. Generally, 3 to 4 dilatations are required for each region of stenosis. Balloon inflation is maintained for 30 to 90 seconds during each dilatation, depending upon anatomic considerations and operator preference.

Following the final dilatation, the guidewire and balloon catheter are withdrawn leaving the guiding catheter in place. Selective coronary angiography then is performed to evaluate the cosmetic appearance of the vessel following the angioplasty and to determine the severity of the residual stenosis.

Balloon angioplasty, while an effective method for treating clogged arteries, has several known side effects. For instance, the enlarging of the artery and removal of the atherosclerotic plaque from the lumen can weaken the artery wall, potentially causing the wall to collapse. Furthermore, injury to the artery wall can cause scarring of the wall and subsequent incomplete healing of the endothelial wall. The scarred portions of the artery wall can then act as a site for rebuilding of the occluding plaque and reclogging of the affected artery. This reclogging process is called restenosis. The aforementioned side effects have been known to lead to a nearly 40% rate of restenosis following balloon angioplasty procedures and, thus, the need for additional expensive medical procedures.

Numerous methods for treating these side effects have been attempted. Molecular biology, drug therapy, the use of anti-platelet receptor anti-bodies, and the use of anti-sense oligonucleotides are the most common treatment procedures. Unfortunately, these methods can be prohibitively expensive. Moreover, studies show that such procedures do not significantly reduce the occurrence of restenosis.

Currently under investigation are various forms of radiation therapy. Under this proposed treatment, radioactive stents are used in healing the affected artery. This procedure has side effects as well, however. For example, the artery can potentially weaken following the treatment. More significantly, the prolonged exposure to radiation can be dangerous for attending hospital personnel and possibly lead to the development of cancer in the patient. In addition, stents have been known to cause abrupt thrombotic closure and hemorrhaging. The stents, themselves, can even become sites for the lodging and growth of resistant bacteria.

The application of laser beam energy in the treatment of medical conditions is known. Low power lasers, e.g., lasers having an energy output on the order of one milliwatt to 100 milliwatts and varying wavelengths, have been used since 1969 for medical and dental applications which include wound healing. Low level laser beam energy has been shown to enhance wound healing and reduce the development of scar tissue following surgical procedures, relieve stiff joints and promote the healing of injured joints, stimulate the body's ability to heal fractures and large contusions as well as enhancing the healing of difficult, slow-to-heal or non-healing decubitus or diabetic ulcers in patients.

Recent research has shown that the use of low power red laser light on rabbit aortas stimulates the wound-healing process following balloon angioplasty. The application of red laser light was shown to prevent the adverse balloon-induced changes that can occur, including neointimal smooth muscle cell proliferation. In addition, the application of laser energy to the affected area increased the rate and completeness of endothelial wall regeneration, thus resulting in a decreased rate of restenosis.

At present, however, there is no cost-effective device for the safe delivery of low power laser energy to arteries following balloon angioplasty. Accordingly, a need exists for an apparatus for applying low level laser energy to an affected artery following balloon angioplasty treatment. More particularly, a need exists for a cost-effective apparatus for applying the low level laser energy to the affected artery that will reduce weakening and collapse of the vessel, reduce neointimal smooth muscle cell proliferation, increase the rate of endothelial wall regeneration, reduce scarring of the vessel wall, and decrease or eliminate the rate of restenosis following balloon angioplasty treatment.

SUMMARY OF THE INVENTION

The present invention provides an apparatus for applying low level laser energy to an affected vessel following balloon angioplasty treatment. The present invention satisfies the need for a cost-effective method of laser treatment that reduces the current rate of restenosis following the treatment.

In a preferred embodiment, the apparatus of the present invention employs a catheter to be inserted into a vessel, such as an artery. An inflatable balloon surrounds a portion of the catheter near a distal end of the catheter. The catheter is connected to a tube which provides inflation fluid for inflating the balloon. A flexible pleated sleeve of clear silicone surrounds the balloon. Electrically conductive flexible film strips are embedded in the sleeve. The strips are aligned longitudinally along the outside of the balloon. Each strip contains a plurality of vertical cavity lasers connected in series. Power is provided to the lasers via an external power source so that each VCSEL emits approximately 1 to 10 milliwatts of power.

In a second embodiment of the apparatus of the present invention, a non-expanding catheter is utilized. An electrically conductive flexible strip is positioned along the sides and the top and bottom of the catheter. The lasers are connected in series to an external power source which provides low level power to each laser.

The present invention solves the problems of the prior art by providing a convenient, efficient, and effective mechanism for delivering laser beam energy for the purposes of treating an affected area of an artery wall. During the balloon angioplasty treatment, the device is inserted into the vessel and the balloon is expanded. The flexible sleeve surrounding the balloon expands to accommodate the balloon. The longitudinally-aligned electrically conductive flexible strips remain disposed along the top, bottom, and sides of the balloon when inflated. When power is applied to the lasers, low level laser energy is transmitted to the vessel continuously for five to ten minute periods. Thus, the present invention does not require a sophisticated and expensive mechanism for delivering the laser energy directly to the affected area.

By providing a device for applying low level laser energy to the treated artery, which energy is known to decrease neointimal smooth muscle cell proliferation and stimulate the wound-healing process, the rate of restenosis can be decreased. Further, by stimulating the wound healing process, such treatment can also help to reduce the additional attendant side effects associated with the balloon angioplasty treatment.

A more complete understanding of the laser balloon angioplasty apparatus of the present invention will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

Figure 1:
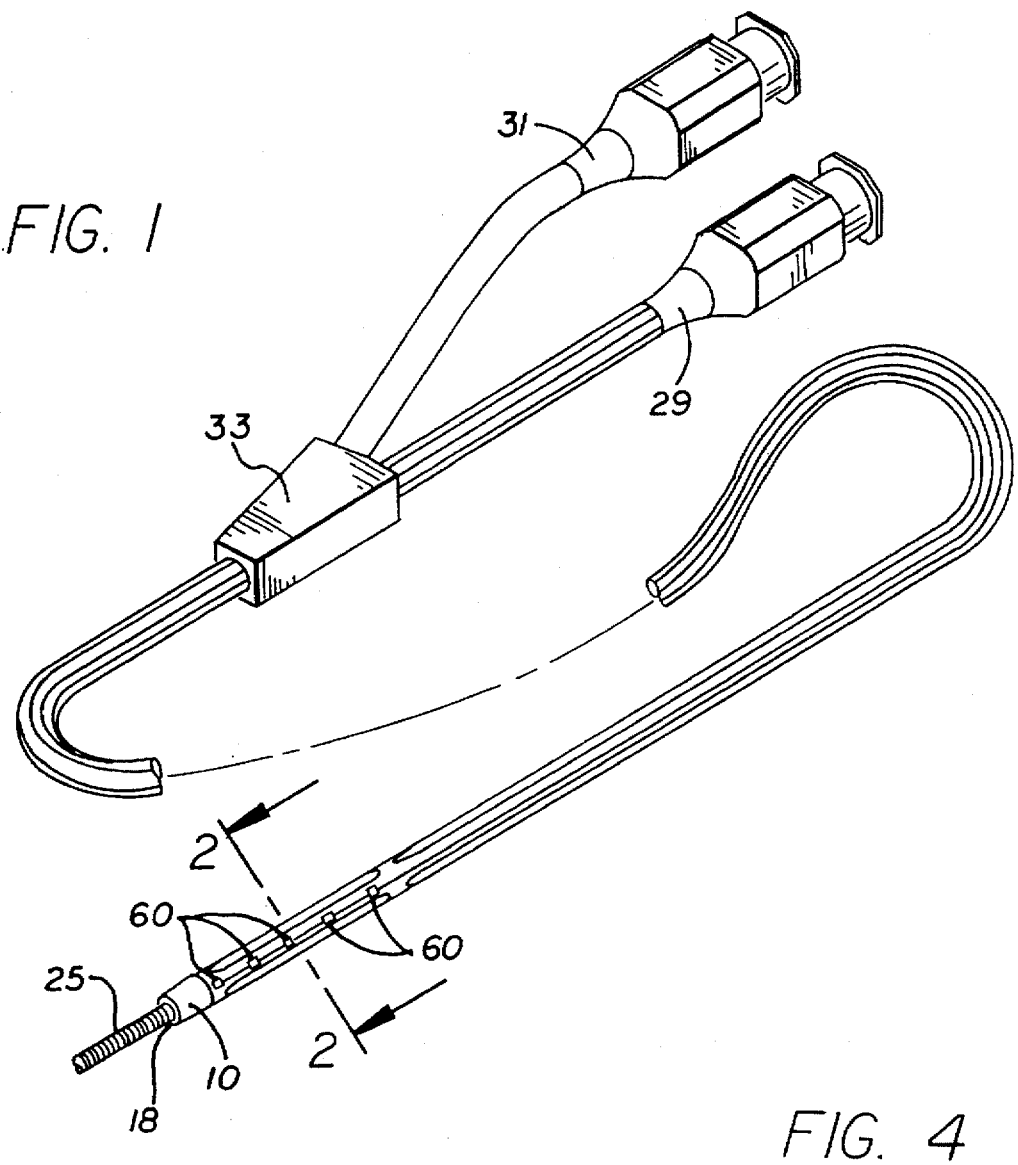
FIG. 1 is a perspective view of a preferred embodiment of the catheter of the present invention.

FIGS. 1-4 illustrate a first preferred embodiment of the present invention. It should be understood that the following discussion of the presently preferred embodiments is not to be considered in a limiting sense. Rather, it is to be understood that numerous modifications, additions, and/or substitutions can be made to the preferred embodiments without departing from the spirit and scope of the present invention.

A laser balloon angioplasty device in accordance with the first preferred embodiment of the present invention includes a catheter 12 having a housing 10 extending from a proximal end (not shown) to a distal end 18. The housing 10 is generally cylindrical and is comprised of flexible plastic or a similarly resiliently flexible material. The distal end 18 of the housing 10 is made in accordance with a dual lumen design. The space between the inner wall 15 of the housing and the outer edge 17 of the guidewire 25 defines a dual guidewire/inflation lumen 30 having a guidewire 25 therein. The dual lumen 30 is generally annular in cross section. The guidewire 25 is comprised of stainless steel or platinum or an equivalent thereof.

As shown in FIG. 1, the catheter 12 includes a tube 29 that provides inflation fluid to the balloon 35. Inflation fluid is evacuated through tube 31. The inflation tube 29 and evacuation tube 31 combine at junction box 33 to communicate with the dual lumen 30. The dual lumen 30 communicates with the interior of a balloon 35 located near the distal end 18 of the catheter. The balloon 35 typically is formed from an inelastic material to permit uniform inflation to a predetermined volume. The balloon 35, when inflated with inflation fluid fed from an inflation tube 37 that communicates with the dual lumen 30, expands to apply therapeutic outward pressure against the interior walls of an occluded blood vessel in which the balloon 35 is positioned. Inflation fluid is removed utilizing a removal tube 39 that communicates with the dual lumen 30.

The wall thickness of the housing 10 is approximately 0.002-0.003 inches. The total outside diameter of the balloon catheter, other than in the region of the balloon 35 itself, is about 0.040 inches. The balloon catheter is made of synthetic material such as nylon.

Figure 2:
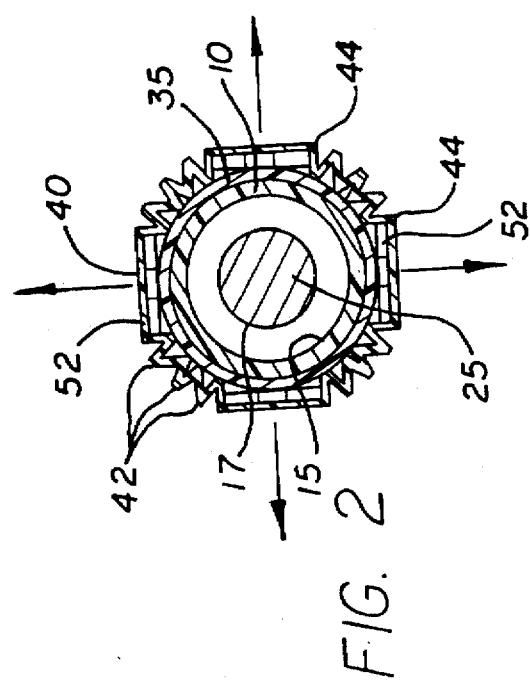
FIG. 2 is a front view of the catheter of the present invention.

As shown in detail in FIG. 2, a flexible sleeve 40 surrounds the balloon 35 near the distal end 18 of the catheter. The sleeve 40 has a thickness of approximately 0.25-0.50 mm and is preferably formed of optically transparent soft silicone or a similar material. The sleeve 35 is molded to accommodate balloon catheters of different sizes. When the balloon 35 is not inflated, the sleeve 40 fits tightly over the balloon 35. The sleeve 40 contains flat portions 44 along the top, bottom, and sides of the balloon to accommodate conductive strips 52 embedded therein. To accommodate the expansion of the balloon 35, the sleeve 40 contains pleats 42. When the balloon 35 is in its expanded state (shown in FIG. 4), the pleats 42 expand to permit the flat portions 44 of the sleeve 40 to maintain the same orientation with respect to the balloon 35 as in the uninflated state. The transparent soft silicone material permits the transfer of laser energy therethrough, as described below.

Four electrically conductive flexible film strips 52 are embedded into the flat rectangular portions of the sleeve 40 adjacent to the balloon 40. Each electrically conductive film strip has a thickness of approximately 0.003 inches. The strips 52 are aligned longitudinally along the outer circumference of the balloon 35. Accordingly, the length of each strip is approximately the same length as the balloon. This length will vary depending upon the length of the balloon. Each strip 52 is preferably formed of a polyester conductive material, such as Kapton or Ultem. In the uninflated state, the conductive film strips are aligned along the top, bottom, and sides of the balloon in the flat portions 44 of the sleeve 40. When the balloon 35 is filled with inflation fluid via the distal inflation lumen 30, the flexible nature of the sleeve allows the conductive film strips to maintain this orientation. Each strip 52 is electrically conductive and includes electrical interconnections etched along the surface. The various interconnections permit the surface-mounting of various electrical devices on the strip 52.

Up to 8 vertical surface-emitting laser ("VCSELs") chips 60 are surface-mounted onto each strip 52. Each chip 60 is approximately 2 millimeters long and the chips 60 are spaced approximately 3 millimeters apart along the surface of each strip 52. Each 2 millimeter long VCSEL chip 60 contains up to 8 VCSEL laser wells. Each laser has a nominal operating power output of 2.6 milliwatts and a wavelength on the order of 600–800 nanometers, with the preferred wavelength being approximately 780 nanometers. The preferred power output of each VCSEL ranges from 1 to 8.2 milliwatts. However, the inventor has found that 4 milliwatts represents a preferred operating level that affords sufficient power for laser treatments having a duration of 5–10 minutes.

Vertical cavity surface-emitting lasers are known and comprise lasers which emit a collimated beam normal to the surface of the semiconductor substrate. The semiconductor typically comprises aluminum arsenide (AlAs) or gallium arsenide (GaAs), or a combination thereof. Each VCSEL has a self-contained, high-reflectivity mirror structure forming a cavity which produces a collimated beam. While particular applications of the present invention may require a more focused or less focused beam, the preferred embodiment uses the beam directly from the VCSELs. The beam may be further focused or defocused utilizing a microlens incorporated into the VCSEL. A typical VCSEL may be on the order of 300 micrometers long.

Figure 3:
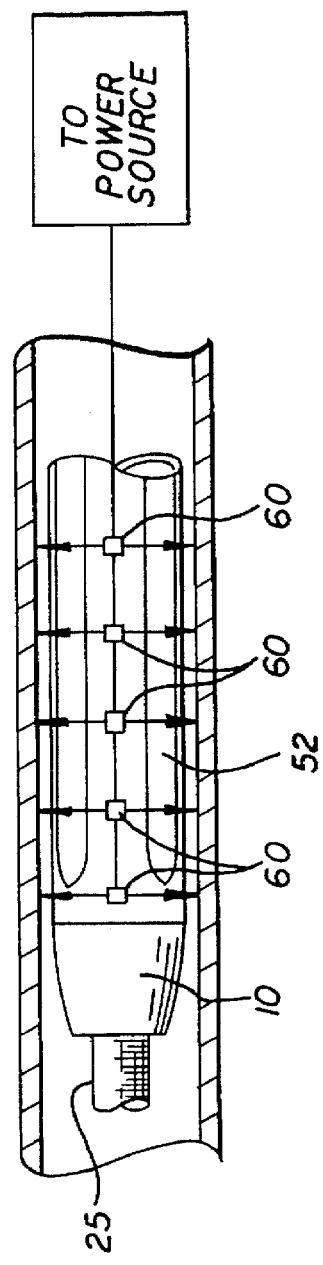
FIG. 3 is a side view of the catheter of the present invention with the balloon in the unexpanded state.

The VCSEL chips 60 are disposed on each conductive film strip 52 as shown in FIG. 3. Each strip 52 contains 4–8 VCSEL chips spaced 3 millimeters apart and connected through the sleeve 40 to an external power source 72 via a lead 62. The chips of VCSELs are interconnected with flexible electrical connectors etched on the strip 52. Preferably, the VCSEL chips 60 in each strip 52 would be electrically connected in series.

Figure 6:
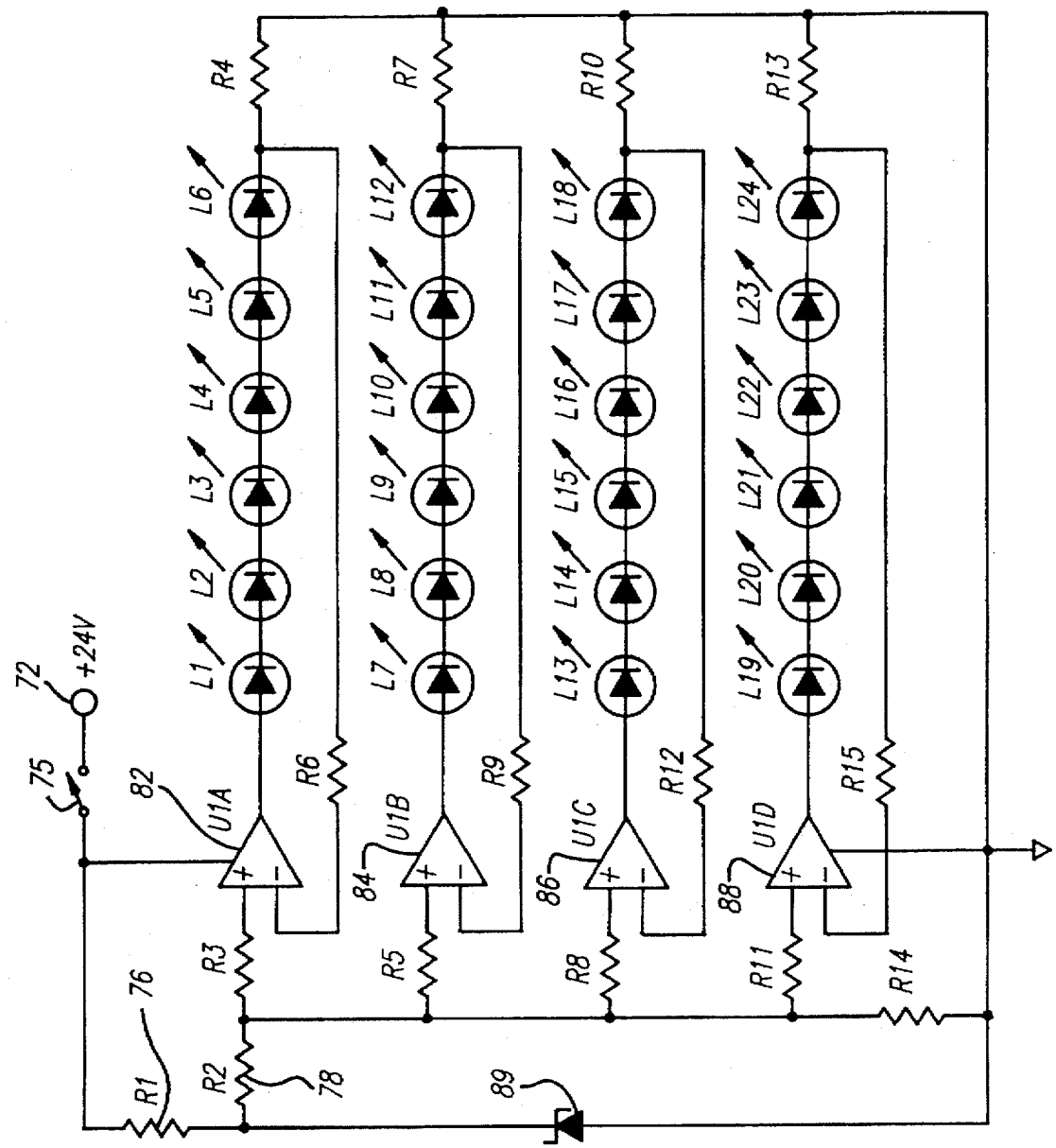
FIG. 6 is a circuit diagram of a laser therapy control circuit utilized with the catheter of the present invention.

A preferred embodiment of a laser angioplasty therapy control circuit 70 is shown in FIG. 6. As shown, an external power source 72 supplies a potential of 3 volts to the circuit via a switch 75. The power source 72 is connected through switch 75 to resistors 76, 78. The voltage is regulated through resistors 76, 78 which regulate the voltage to noninverting operational amplifiers 82, 84, 86, 88. Op-amps 82, 84, 86, 88 regulate voltage to VCSELs 60. The voltage is further regulated by zener diode 89. Other types of power control circuits that can be utilized are shown, for example, in U.S. application Ser. Nos. 08/136,382 and 08/215,263, both by M. Prescott, filed Oct. 12, 1993 and Mar. 21, 1994, respectively, the disclosure of which are hereby incorporated by reference.

Figure 4:
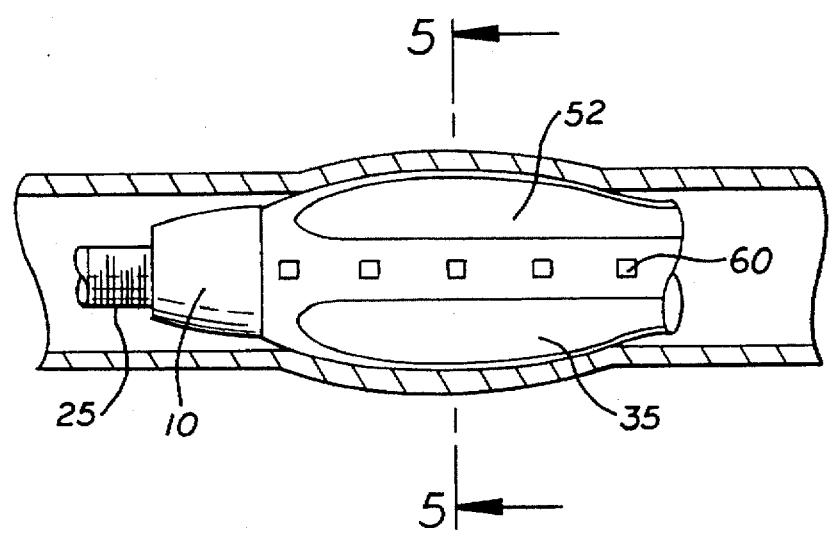
FIG. 4 is a side view of the catheter of the present invention with the balloon in an expanded state.
Figure 5:
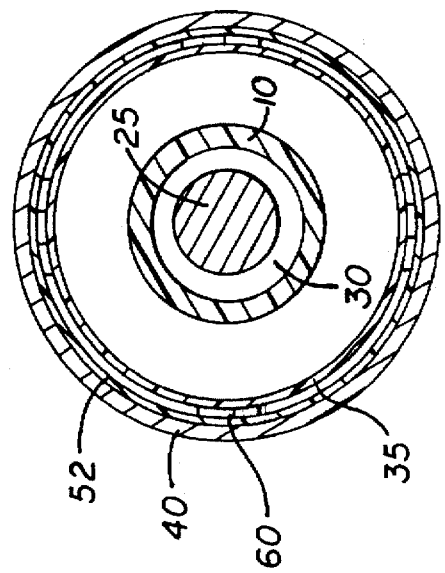
FIG. 5 is a forward view of the catheter of the present invention with the balloon in an expanded state.

The laser balloon angioplasty treatment is performed by inserting the balloon angioplasty device into the affected artery proximate the region of stenosis. In the uninflated state, the strips 52 are aligned along the top, bottom, and sides of the balloon 35. Inflation fluid is provided through the inflation lumen 30 to the balloon 35. As the balloon 35 fills with fluid, it gradually expands to open the artery near the region of stenosis. While the balloon 35 is expanded, as shown in FIG. 5, the switch 75 is activated to provide power to the laser therapy control circuit 70. As shown in FIG. 4, the VCSEL strips 52 remain aligned along the top, bottom, and sides of the balloon 35 in the flat portions 44 of the sleeve 40. The VCSELs contained in each VCSEL chip 60 emit a low power laser beam through the optically clear silicone sleeve 40. The low power laser energy is preferably to be applied for a period of five to ten minutes. The laser energy stimulates the affected area to improve healing and reduce restenosis and neointimal smooth muscle cell proliferation.

A second embodiment of the present invention is described, but not shown. In this embodiment, a non-expandable catheter having distal and proximal ends is utilized. A flexible sleeve surrounds the catheter near the distal end of the catheter. Four electrically conductive flexible strips surround the catheter and are embedded in the flexible sleeve. The strip contains VCSEL chips embedded therein throughout its area. The configuration of the VCSEL chips are similar to the VCSEL chips described with respect to the first embodiment. Each VCSEL has a nominal power output of 2.6 milliwatts and a wavelength on the order of 600–800 nanometers, with the preferred wavelength being approximately 780 nanometers. Preferably, the VCSEL chips in the strip would be electrically connected in series.

Having thus described a preferred embodiment of a laser balloon angioplasty device, it should be apparent to those skilled in the art that certain advantages of the within system have been achieved. It should also be appreciated that various modifications, adaptations, and alternative embodiments thereof may be made within the scope and spirit of the present invention. For example, a circuit has been shown that delivers constant voltage to the VCSELs, but it should be apparent that the inventive concepts described above would be equally applicable to a pulsed mode method of delivery. Furthermore, a dual lumen design has been illustrated in the first embodiment, but it should be apparent that the concepts described above would be equally applicable to a balloon device utilizing a coaxial lumen design of the second embodiment and vice-versa. The invention is further defined by the following claims.

What is claimed is:

1. A balloon catheter extending from a proximal end to a distal end, the catheter comprising:

a guidewire disposed within the catheter;

an inflatable balloon surrounding a portion of the guidewire proximate the distal end of the catheter;

means for inflating the balloon connected to the balloon;

a flexible sleeve surrounding the balloon;

a first electrically conductive flexible strip arranged longitudinally adjacent a portion of the balloon and embedded within the sleeve;

a first plurality of vertical cavity surface-emitting lasers disposed on a surface of the conductive strip; and means for delivering power to the vertical cavity lasers.

2. The balloon catheter, as recited in claim 1, further comprising:

a second electrically conductive flexible strip arranged longitudinally adjacent a portion of the balloon and disposed opposite the conductive strip within the sleeve; and a second plurality of vertical cavity surface-emitting lasers disposed on a surface of the second conductive strip.

3. The balloon catheter, as recited in claim 2, further comprising:

a third electrically conductive flexible strip arranged longitudinally adjacent a portion of the balloon and disposed between the first conductive strip and the second conductive strip within the sleeve;

a third plurality of vertical cavity surface-emitting lasers disposed on a surface of the third conductive strip;

a fourth electrically conductive flexible strip arranged longitudinally adjacent a portion of the balloon and disposed opposite the third conductive strip within the sleeve; and a fourth plurality of vertical cavity lasers disposed on a surface of the fourth conductive strip.

4. The balloon catheter, as recited in claim 3, wherein the flexible sleeve is pleated.

5. The balloon catheter, as recited in claim 4, wherein the flexible sleeve is comprised of optically clear silicone.

6. The balloon catheter, as recited in claim 4, wherein the first conductive strip is comprised of polyester.

7. The balloon catheter, as recited in claim 4, wherein each vertical cavity laser includes a microlens.

8. The balloon catheter, as recited in claim 4, wherein the means for delivering laser energy comprises an external power source connected in series to the vertical cavity lasers.

9. The balloon catheter, as recited in claim 8, wherein less than 8 milliwatts of power are emitted by each vertical cavity surface-emitting laser.

10. The balloon catheter, as recited in claim 4, wherein the means for inflating the balloon further comprises:

a lumen in fluid communication with the balloon; and means for delivering inflation fluid to the balloon through the lumen.

11. A balloon catheter extending from a proximal end to a distal end, the catheter comprising:

a guidewire disposed within the catheter;

an inflatable balloon surrounding a portion of the guidewire proximate the distal end of the catheter;

means for inflating the balloon;

a flexible sleeve surrounding the balloon;

a plurality of conductive strips arranged longitudinally adjacent a portion of the balloon and embedded within the sleeve;

a plurality of vertical cavity surface-emitting lasers disposed in each of the conductive strip; and means for delivering power to the vertical cavity lasers.

12. The balloon catheter, as recited in claim 11, wherein the flexible sleeve is comprised of clear silicone.

13. The balloon catheter, as recited in claim 11, wherein each of the conductive strip is comprised of polyester.

14. The balloon catheter, as recited in claim 11, wherein each vertical cavity surface-emitting laser further includes a microlens.

15. The balloon catheter, as recited in claim 11, wherein the means for delivering laser energy comprises an external power source connected to the vertical cavity lasers.

16. The balloon catheter, as recited in claim 15, wherein less than 8 milliwatts of power are emitted by each vertical cavity laser.

17. A balloon catheter extending from a proximal end to a distal end, the catheter comprising:

a guidewire disposed within the catheter;

an inflatable balloon surrounding a portion of the guidewire proximate the distal end of the catheter;

means for inflating the balloon connected to the balloon;

a flexible sleeve surrounding the balloon;

an electrically conductive flexible strip surrounding a portion of the balloon and embedded within the sleeve;

a plurality of vertical cavity surface-emitting lasers disposed on a surface of the conductive strip; and means for delivering power to the vertical cavity lasers.

18. The balloon catheter, as recited in claim 17, wherein the flexible sleeve is comprised of optically clear silicone.

19. The balloon catheter, as recited in claim 17, wherein each of the conductive strip is comprised of polyester.

20. The balloon catheter, as recited in claim 17, wherein each vertical cavity surface-emitting laser includes a microlens.

21. The balloon catheter, as recited in claim 17, wherein the means for delivering laser energy comprises an external power source connected to the vertical cavity lasers.

22. The balloon catheter, as recited in claim 20, wherein less than 8 milliwatts of power are emitted by each vertical cavity laser.

* * * * *